United States Patent [19]

McDonald

[11] Patent Number: 5,006,115
[45] Date of Patent: Apr. 9, 1991

[54] NEEDLE PLACEMENT SENSOR
[75] Inventor: Ray S. McDonald, St. Paul, Minn.
[73] Assignee: Medtronic, Inc., Minneapolis, Minn.
[21] Appl. No.: 385,131
[22] Filed: Jul. 25, 1989
[51] Int. Cl.⁵ .............................................. A61M 25/00
[52] U.S. Cl. ........................................ 604/175; 604/93
[58] Field of Search ....................... 604/93, 175, 8–10, 604/131, 891; 116/DIG. 17, 205

[56] References Cited

U.S. PATENT DOCUMENTS

| | | | |
|---|---|---|---|
| 4,692,146 | 9/1987 | Hilger | 604/93 |
| 4,760,837 | 8/1988 | Petit | 604/93 |
| 4,832,054 | 5/1989 | Bark | 604/93 |

*Primary Examiner*—Stephen C. Pellegrino
*Assistant Examiner*—Ralph A. Lewis
*Attorney, Agent, or Firm*—S. A. Kassatly; Robert J. Klepinski; Reed A. Duthler

[57] ABSTRACT

An implantable medical device having a main body, and a port in the main body for receiving a medical instrument percutaneously. A resilient dome is mounted in the device for communicating with the medical instrument, and for flexing from a first rest position to a second position after contact with the medical instrument. The dome provides an extra corporeal response signal resulting from the flexion of the dome from the first position to the second position.

4 Claims, 1 Drawing Sheet

1

NEEDLE PLACEMENT SENSOR

FIELD OF THE INVENTION

The present invention relates to the sensing of needle position within a medical device, particularly the invention of the needle into an implanted medication reservoir.

BACKGROUND OF THE INVENTION

Various types of implantable medical devices are in use for dispensing medication within the body. These devices either have reservoirs which are to be filled for dispensation on a time-release basis, such as an implantable drug dispenser, or have ports for insertion of medication which is dispensed through an implantable catheter, commonly known as a catheter access port. In these devices, the reservoir for receiving medication is commonly sealed with a pierceable septum. A hypodermic needle is inserted through the skin and through the septum into the reservoir. Once within the reservoir, the medication is dispensed from the syringe.

It is critical to the performance of this process that the needle tip is properly positioned at the desired dispensing location. If the needle is outside the device, medication will improperly be dispensed to the body. If the needle opening is within the septum, excess pressure in the syringe may be required to dispense medication or the dispensing may be entirely prevented. Techniques have been tried to sense needle placement involving complex apparatus for determining needle placement. What is needed is self-contained apparatus for sensing when the needle has reached the bottom of the reservoir, which does not require intricate equipment.

SUMMARY OF THE INVENTION

According to the present invention, a drug receiving reservoir in a mechanical device includes means for providing tactile or audible feedback upon proper contact with a hypodermic needle. In the preferred embodiment, the means for providing feedback is a dome-shaped element in the septum having a first raised position for contact with the approaching needle and a second position after being pressed by the needle. The device includes means for producing tactile feedback and an audible sound in its transition from the first and second position.

DETAILED DESCRIPTION OF THE PREFERRED EMBODIMENTS

Figure 1:
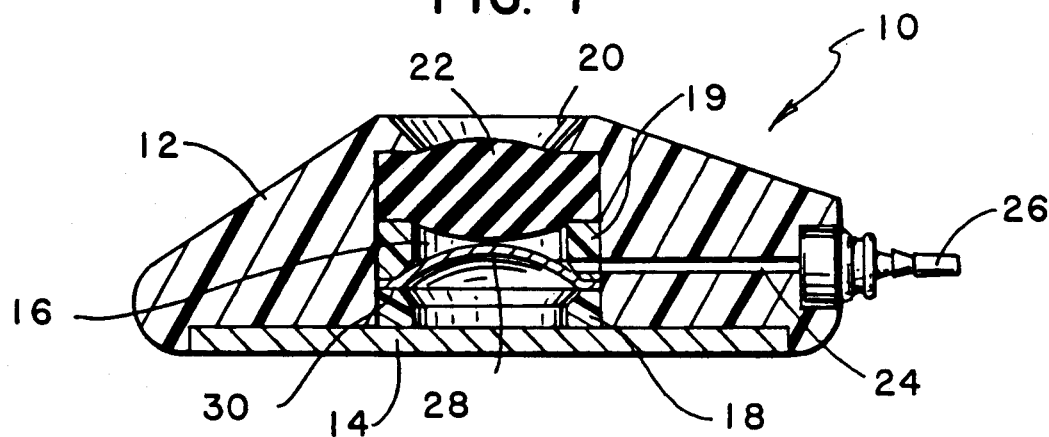
FIG. 1 illustrates a side cross-sectional view of a catheter access port embodying the present invention.

The present invention may be employed in various medical devices by those skilled in the art by the teachings herein. For purposes of explanation, the invention is illustrated in terms of the catheter access port 10. Catheter access port 10 includes a main body 12 which is generally in the shape of conical frustrum. Fitted into the bottom of body 12 is base 14. Within body 12 is a medication reservoir 16 having two generally cylindrical wall segments 18 and 19. A top surface of body 12 is provided with a needle access 20. A pierceable septum 22 seals reservoir 16 from needle access 20. A drug outlet 24 connects reservoir 16 with the outside of body 12 through catheter connector 26. Mounted in wall segments 18 and 19, within reservoir 16, is means for providing feedback to needle insertion, which in this case is a dome 28. In the illustrated embodiment, dome 28 has a annular ring 30 around its edge. Will segments 18 and 19 capture annular ring 30 to hold dome 28 in place.

In FIG. 1, dome 28 is illustrated in a first position at rest.

Figure 2:
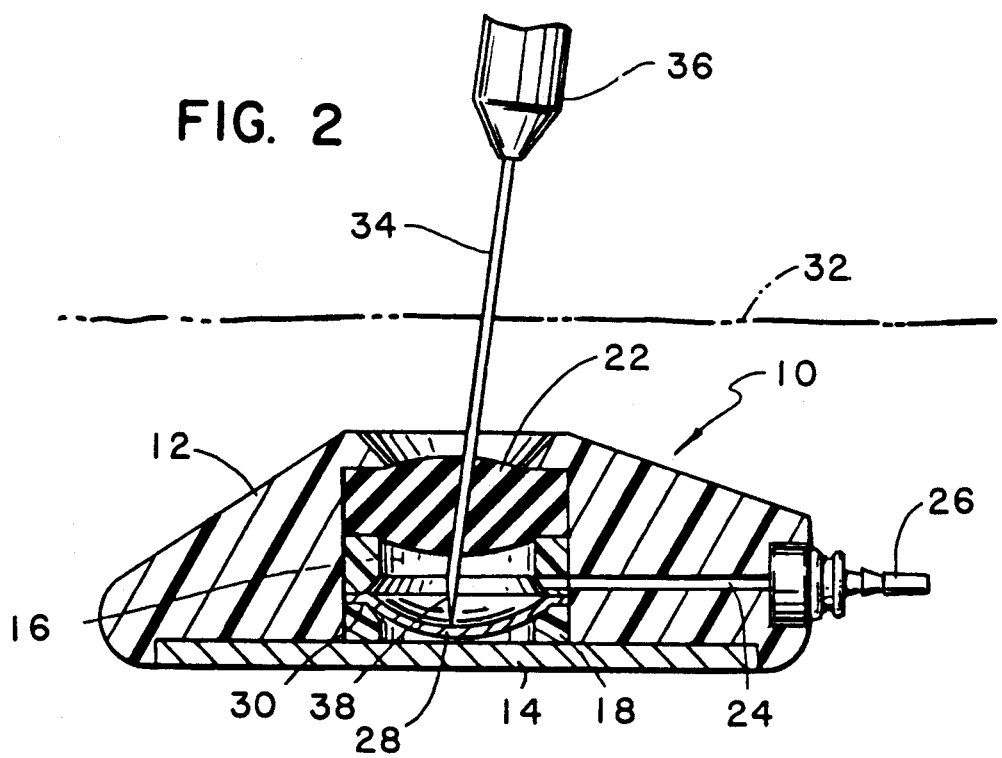
FIG. 2 shows the access port of FIG. 1 showing the syringe in place after activating a device according to the present invention.

FIG. 2 illustrates CAP 10 implanted in the body below skin 32. Needle 34 of syringe 36 is inserted through skin 32 and through septum 22 into reservoir 16. Needle 34 has a beveled tip 38.

In FIG. 2, dome 28 is shown in a second depressed position after being pressed downward by tip 38 of needle 34. Once needle 34 is positioned within reservoir 16, the medication can be dispensed from syringe 36 out through tip 38 into reservoir 16.

Dome 28 is designed to snap between the first position and the second position. Dome 28 is chosen of suitable material, such as metals, which will provide an audible signal of the transfer from the first position to the second position. Additionally, the holder of syringe 34 will feel the resistance of first touching dome 28 in its first position and the snap as dome 28 gives and moves to the second position as illustrated in FIG. 2. Thus, both audible and tactile response are provided.

Dome 28 may also be constructed of non-metallic material such as plastics. Those skilled in the art may select from the various snapping domes which will accomplish the desired audible or tactile signal for creation.

Some suitable examples of materials are titanium, stainless steel, polyethylene and teflon.

Figure 3:
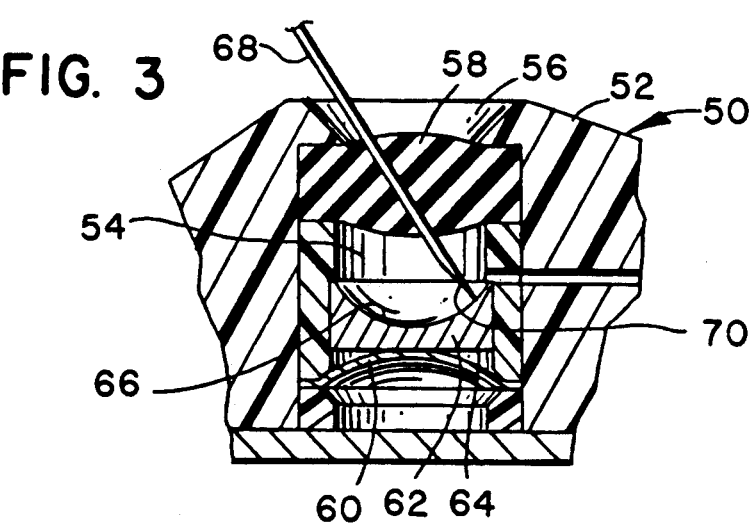
FIG. 3 shows an alternative embodiment of the present invention.

An alternative embodiment of the present invention is illustrated in FIG. 3 where a medical device 50 includes a body 52 encasing a reservoir 54. A needle access 56 is provided in the top of body 52. Reservoir 54 is sealed from needle access 56 by septum 58. Mounted within reservoir 54 is dome 60 which operates in a manner similar to dome 28 described above. A piston 62 is mounted in reservoir 54 above dome 60. Piston 62 has a bottom surface 64 suitable for contacting and pushing against dome 60 to move it from a first position as illustrated to a second lower position as discussed above. Piston 62 has an upper concave surface 66. Piston 62 is slidable within reservoir 54.

In this embodiment, a needle 68 which pierces septum 58 will contact surface 66 of piston 62. The beveled tip 70 of needle 68 is shown in contact with surface 66 at an angle to perpendicular. It is not always possible to exactly align a needle in a right angle to the bottom surface of reservoir 54. Concave surface 66 will urge tip 70 downwards to the center of surface 66, as pressure is applied. In the present embodiment, as needle 68 is pushed in, tip 70 centers on concave surface 66 and slides piston 62 downward against dome 60. As piston 62 is urged downward, piston 60 moves from its first position to a second lower position, providing the tactile and audible response discussed above.

Piston 62 is preferably designed of material such as alloyed or unalloyed titanium or 300 series stainless steel. The choice of material should be one that will not be punctured by tip 70, but which will be resilient enough to prevent bending of tip 70 if excess pressure is applied to needle 68.

While the invention is shown in view of a preferred embodiment, various medical devices which require subcutaneous contact with a probing instrument may employ the present invention. Unlike the prior art difficulties encountered with complex solutions, the present invention provides both means for audible response and tactile response to insertion of a probe in an implantable medical device.

What is claimed is:

1. An implantable medical device comprising:
   a device body;
   port means in said device body for receiving a medical instrument percutaneously; and
   means, mounted in the device for communication with the medical instrument for flexing from a first rest position to a second position after contact with the medical instrument, and for providing an extracorporeal response signal resulting from the flexion from the first position to the second position.

2. The device of claim 1 wherein said flexing means provides an audible response to the movement from the first to the second position.

3. The device of claim 1 wherein said flexing means provides a tactile response to the movement from the first to the second position.

4. An implantable device comprising:
   a reservoir;
   means for receiving a needle for insertion of liquid in the reservoir;
   a dome mounted in the reservoir having a first rest position and a second depressed position, the dome designed for movement between the first and second position upon needle contact, the dome providing an audible response to the movement of the first to the second position.

* * * * *